United States Patent [19]

Blum et al.

[11] Patent Number: 5,189,064

[45] Date of Patent: Feb. 23, 1993

[54] TREATMENT OF COCAINE ADDICTION

[75] Inventors: Kenneth Blum, San Antonio; Michael C. Trachtenberg, Houston, both of Tex.

[73] Assignee: Matrix Technologies, Inc., Houston, Tex.

[21] Appl. No.: 523,300

[22] Filed: May 14, 1990

Related U.S. Application Data

[63] Continuation of Ser. No. 105,353, Oct. 7, 1987, abandoned, which is a continuation-in-part of Ser. No. 757,733, Jul. 22, 1985, Pat. No. 4,761,429.

[51] Int. Cl.$^5$ .......................................... A61K 31/195
[52] U.S. Cl. .................................... 514/561; 514/810; 514/811; 514/812
[58] Field of Search ................ 514/561, 810, 811, 812

[56] References Cited

U.S. PATENT DOCUMENTS

| | | | |
|---|---|---|---|
| 4,312,857 | 1/1982 | Coy et al. | 424/154 |
| 4,357,343 | 11/1982 | Madsen et al. | 514/400 |
| 4,439,452 | 3/1984 | Ehrenprise et al. | 514/561 |

FOREIGN PATENT DOCUMENTS 8203551  10/1982  World Int. Prop. O. .......... 514/811

OTHER PUBLICATIONS

Bain, et al.; Life Sciences 40:1119-1125 (1986); Naloxone Attenuation of the Effect of Cocaine on Rewarding Brain Stimulation.
Schwartz, et al.; Neuropharmacology 17:665-685 (1978); Modulation of Receptor Mechanisms in the CNS:Hyper and Hyposensitivity to Catecholamines.
Letter to the Editor; J. Pharm. Pharmac., 24:905-06 (1972); Dopamine turnover in the Corpus Striatum and the Limbic System After Treatment with Neuroleptic and Anti-acetylcholine Drugs.
Reggiani, et al.; Substance and Alcohol Actions/Misuse; 1:151-58 (1980); Role of Dopaminergic-Enkephalinergic Interactions in the Neurochemical Effects of Ethanol.
Mello, et al.; Science; 245:859-862 (1989); Buprenorphine Supresses Cocaine Self-Administration by Rhesus Monkeys.
Misra, et al.; Pain; 28:129-138 (1987); Stereospecific Potentiation of Opiate Analgesia by Cocaine: Predominant Role of Noradrenaline.
Hughes, et al.; Nature; 258:577-579 (1975); Identification of Two Related Pentapeptides from the Brain with Potent Opiate Against Activity.
Li and Chung; Proc. Nat. Acad. Sci.; 73:1145-1148 (1976); Isolation and Structure of an Untriakontapeptide with Opiate Activity from Camel Pituitary Glands.
Hammer; Dept. of Anatomy & Reprod. Biol., Univ. Hawaii School of Medicine; Cocaine Altera Opiate Receptor Binding in Critical Brain Reward Regions (1976).
Tennant & Sagherian, Double-Blind Comparison of Amantidine and Bromocriptine for Ambulatory Withdrawal from Cocaine Dependence, Arch. Intern. Med., 147:109-112, (Jan. 1987).
Rosen, et al., Clinical Trial of Carbidopa Combination for Cocaine Abuse, Am. J. Psychiatry, 143:1493 (Nov. 1986).
Reith, et al., Sodium-Independent Binding of $^3$H Cocaine in Mouse Striatum is Serotonin Related, Brain Research, 342(1): 145-148 (1985).
Moir & Eccleston, The Effects of Precursos Loding in the Cerebral Metabolism of 5-Hydroxyindoles, J. Neurochem., 15:1093-1108 (1968).
Biggio, et al., Stimulation of Dopamine Synthesis in Caudate Nucleus by Intrastriatial Enkephalins and Antagonism by Naloxone, Science, 200:552-54 (May 1978).
Clouet, A Biochemical and Neurophysicalogical Comparison of Opioids and Antipsychotics, Annals New York Acad. of Sci., 398:130-137 (1982).
Dackis, et al., Bromocriptine Treatment for Cocaine Abuse: The Dopamine Depletion Hypothesis, Int'l. J. Psychiatry in Med., 15(2): 125-135 (1985).
Dackis, et al., New Concepts in Cocaine Addiction: The Dopamine Depletion Hypothesis, Science and Behavioral Reviews, 9:469-477 (1985).
Clouet, et al., Catecholamine Bisynthesis in Brains of Rats Treated with Morphine, Science, 168:854-855 (1970).
Gold, et al., New Insights and Treatments: Opiates Withdrawal and Cocaine Addiction, Clinical Therapeutics, 7(1): 6-21 (1984).
Verebey, et al., in Psychopharmacology of Cocaine: Behavior Neurophysiology, Neurochemistry and Proposed Treatment, Psychopharmacology: Impact on Clinical Psychiatry, 219-245, (1985).
Rosecran, Abstract, VII World Congress of Psychiatry, Vienna, Australia (1985).
Schwartz, et al., Fourth World Congress on Biological Psychiatry 418, No. 600.2 (1985).
Gessa, et al. 4th World Congress on Biological Psychiatry, 459 No. 620.10 (1985).
Mindell, Earl Mindell's Shaping up with Vitamins, pp. 162-163; 172-173 (1985).
The Nutrition Desk Reference, pp. 220-224 (1985).
Physician's Desk Reference, 35 Ed. (1981), p. 1102.

Primary Examiner—S. J. Friedman
Attorney, Agent, or Firm—Iver P. Cooper

[57]         ABSTRACT

Cocaine addiction is treated by administration of an endorphinase or enkephalinase inhibitor, and optionally, a dopamine precursor, or a serotonin precursor, a GABA precursor, or an endorphin or enkephalin releaser. These components promote restoration of normal neurotransmitter function and are non-addictive. Use of the dopamine precursors L-phenylalanine or L-tyrosine, the enkephalinase inhibitor D-phenylalanine and/or the serotonin precursor L-tryptophan is especially preferred.

10 Claims, No Drawings

TREATMENT OF COCAINE ADDICTION

CROSS-REFERENCE TO RELATED APPLICATION

This application is a continuation of U.S. Ser. No. 7/105,353, field Oct. 7, 1987, now abandoned, which is a continuation-in-part of U.S. Ser. No. 06/757,733 filed Jul. 22, 1985, now U.S. Pat. No. 4,761,429.

BACKGROUND OF THE INVENTION

1. Field of the Invention

This invention relates to the use of enkephalinase or endorphinase inhibitors, and, optionally, dopamine precursors, serotonin precursors and/or GABA precursors, in the treatment of cocaine addiction.

2. Information Disclosure Statement

Cocaine is a naturally occurring stimulant derived from the leaves of the coca plant, *Erythroylon coca*. In 1864, cocaine was isolated from the coca leaves.

Coca leaves contain only about one-half of one percent pure cocaine alkaloid. When chewed, only relatively modest amounts of cocaine are liberated, and gastrointestinal absorption is slow. Certainly, this explains why the practice of chewing coca leaves has never been a public health problem in Latin America. The situation changes sharply with the abuse of the alkaloid itself.

The cocaine user experiences three stages of drug effects. The first, acute intoxication ("binge"), is euphoric, marked by decreased anxiety, enhanced self-confidence and sexual appetite, and may be marred by sexual indiscretions, irresponsible spending, and accidents attributable to reckless behavior. The second stage, the ("crash"), replaces euphoria by anxiety, fatigue, irritability and depression. Some users have committed suicide during this period. Finally, the third stage, "anhedonia," is a time of limited ability to derive pleasure from normal activities and of craving for the euphoric effects of cocaine. See Gawin and Kleber, Medical Management of Cocaine Withdrawal, 6–8 (APT Foundation).

In the past, physicians tended to treat primarily the acute symptoms of cocaine abuse, prescribing drugs such as propranolol to treat erratic heart rhythms, diazepam to control convulsions and chlorpromazine to relieve psychosis (paranoia). However, these treatment approaches do not relieve the patient's craving for cocaine.

A number of drugs have been suggested for use in weaning cocaine users from their dependency. Antidepressants, such as lithium and desipramine, were studied by Tennant and Rawson, in PROBLEMS OF DRUG DEPENDENCE 1982, 351-55 (NIDA Res. Monogr. Ser. 43, 1983); Gawin, Psychosomatics, 27: 24–29 (1986); Gawin and Kleber, Arch. Gen. Psychiatry, 41: 903-9 (1984); Kleber and Gawin, J. Clin. Psychiatry 45 (12, Sec. 2): 18-23 (1984).

Certain therapeutic agents are favored by the "dopamine depletion hypothesis." It is well established that cocaine blocks dopamine re-uptake, acutely increasing synaptic dopamine concen&:rations. However, in the presence of cocaine, synaptic dopamine is metabolized as 3-methoxytyramine and excreted. The synaptic loss of dopamine places demands on the body for increased dopamine synthesis, as evidenced by the increase in tyrosine hydroxylase activity after cocaine administration. When the precursor supplies are exhausted, a dopamine deficiency develops. See Dackis and Gold, Neurosc:i. Biobehav. Rev., 9:469-77 (1985); Gold and Dackis, Clin. Therapeutics, 7:6-21 (1984). This hypothesis led to the testing of bromocriptine, a dopamine receptor agonist. Dackis, et al., Int. J. Psychiat. Med., 15: 125-135 (1985); Tennant and Sagherian, Arch. Intern. Med., 147:109 (1987). A second approach was the administration of amantadine, a dopamine releaser. Another approach, also based on this hypothesis, was to provide a precursor for dopamine, such as L-dopa, See Rosen et al., Am. J. Psychiat., 143:1493 (Nov. 1986), or L-tyrosine, Gold, et al., Soc. Neurosci. Absts., 9:157 (1983); Rosecan, Abstract, VII World Congress of Psychiatry, Vienna, Austria (1983);

Agonists are not preferred therapeutic agents. A given agonist may act on several receptors, or similar receptors on different cells, not just on the particular receptor or cell one desires to stimulate. As tolerance to a drug develops (through changes in the number of receptors and their affinity for the drug), tolerance to the agonist may likewise develop. A particular problem with bromocryptine is that it may itself create a drug dependency. It is known that bromocriptine is self-administered by rhesus monkeys. Woolverton, et al., J. Pharm. Exptl. Therap. 230(3): 678-683 (1984).

Releasers are effective only if they have something to release. They will not cure a state of dopamine depletion. Indeed, we would be concerned that dopamine releasers, used alone, would exacerbate the chronic depletion of dopamine.

Precursors use a naturally regulated pathway. The precursor is converted to the neurotransmitter only when needed, and then the body distributes the product on the basis of need. As dopamine is synthesized from precursors such as L-tyrosine, dopamine reserves are rebuilt, thus overcoming the dopamine depletion problem.

Verebey and Gold, in PSYCHOPHARMACOLOGY: IMPACT ON CLINICAL PSYCHIATRY 219-41 (Morgan, ed., 1985) (1985), describe a regimen for the treatment of cocaine addiction that contemplates administration of L-tyrosine, L-tryptophan, thiamine, riboflavin, niacin, pantothenic acid, pyridoxamine, ascorbic acid, folic acid and cyanocobalamin. Their composition does not include any enkephalinase or endorphinase inhibitor or any enkephalin or endorphin releaser. Nor does it include any GABA precursor.

D-phenylalanine is an inhibitor of enzymes involved in the metabolism of endorphins and enkephalins. Ehrenpreis, Subs Alc Act/Mis, 3: 231-239 (1982). It has anti-alcohol craving activity, see copending U.S. application Ser. No. 06/757,733 and counterpart PCT Publ WO 86/01495, and has been studied as a potential antidepressive, Heller, U.S. Pat. No. 4,355,044; Heller in *Modern Pharmacology* 397 (Mosnaim and Wolf, 1978); and analgesic agent, see Ehrenpreis, U.S. Pat No. 4,439,452. There have been no reports of its use in the treatment of cocaine addiction.

L-Tyrosine is a precursor of dopamine see Wurtman, et al., Science, 185: 183-4 (1974); Gibson and Wurtman, Biochem. Pharmacol., 26: 1137-42 (1977). L-tyrosine has been suggested as an anti-depressant. See Gelenberg et al., Am J Psychiat 137:622 (1980).

L-tryptophan is a precursor of serotonin. See Fernstrom and Wurtman, Science, 174: 1023-25 (1971), Eccleston, et al., J. Neurol. Neurosurg. psychiatry, 33: 269-72 (1970). This amino acid has been used to treat food craving. Wurtman, et al., Int., J. Eating Disord. 1: 2-15 (1981); but its effect on craving is uncertain. See Leathwood and pollet, J. Psychiatr. Res., 17: 147-54 (1983). It has also received mixed reviews as an antidepressant. Finally, L-tryptophan has been used to enhance sleep and to reduce pain. See Young, in Nutrition and the Brain, Vol. 7, 49-86 (Wurtman and Wurtman, 1986); Lieberman, et al., J. Psychiatric Res., 17: 135-145 (1983).

L-glutamine is a precursor of the neurotransmitter gamma aminobutyric acid (GABA). L-glutamine has been used to reduce voluntary alcohol consumption in rats. Rodgers, et al., J. Biol. Chem. 214: 503-506 (1955); Ostrovsky, Substance Alcohol Actions/Misuse 5: 247-253 (1984).

No admission is made that any of the foregoing references are prior art, or as to the pertinency of any reference.

SUMMARY OF THE INVENTION

The obsessive drug-seeking behavior demonstrated by cocaine addictt seems to be due to the drug's overwhelming influences on the "reward center" in the brain. In this regard, cocaine is believed to cause an intense stimulation of the reward center, through a "concert" of neurotransmitter events allowing the mood-altering neurotransmitter dopamine to remain active longer than normal. It is this enhanced stimulation, perceived as euphoria, that is repeatedlV sought by cocaine abusers. Our invention breaks the biological hold of cocaine on its victims by pharmacological manipulation of neurotransmitters operating at botlcatecholamine and opioid receptors.

It has now been found that by restoring the function of the neurotransmitter systems implicated in the acute and chronic pharmacological effects of cocaine, the psychological dependence of the patient on cocaine is diminished. It is expected that this treatment will therefore reduce recidivism.

One of cocaine's principal acute effects is the blocking of re-uptake of dopamine, resulting in increased dopamine levels, and dopaminergic transmission and therefore in the euphoria characteristic of the drug. However, chronic use of cocaine leads to dopamine depletion.

This problem, which is the root of the dependence established by cocaine, may be tackled in several ways. In the most general embodiment of this invention, the opioidergic system is used to modulate the dopaminergic system. More specifically, our therapeutic approach is to elevate the levels of the opioid peptides (endorphins and enkephalins) that regulate dopamine synthesis and release.

It is inadvisable however, merely to administer the desired opioid peptides. They are easily degraded in the digestive tract, and are very addictive. Both disadvantages discourage their clinical use.

An alternative approach, which provides the foundation of the present invention, is to elevate endogenous levels of the opioid peptides by inhibiting their destruction by various enzymes. More particularly, brain enkephalin levels are raised by administration of D-phenylalanine, D-leucine, hydrocinnamic acid, or other enkephalinase inhibitors. Similarly, endorphin levels are raised by endorphinase inhibitors such as phenyl methyl sufonyl chloride.

These increase endogenous brain endorphin and enkephalin levels by inhibiting their enzymatic degradation. The endorphins and enkephalins, in turn, regulate synthesis, and release of dopamine. Higher levels of endorphins and enkephalins are associated with higher levels of dopamine. In a preferred embodiment, an endorphin or enkephalin releaser is added.

In another preferred embodiment, a dopamine precursor, such as L-tyrosine or L-phenylalanine, is also administered. If there is a deficit of dopamine, as would be expected in a chronic cocaine user, the body would convert the dopamine precursor directly or indirectly to dopamine, thereby restoring dopamine levels to normal and reducing the feeling of dysphoria inadequate stimulation of the "reward" centers attributable to depressed dopamine levels) which invites readministration of the drug.

In another preferred embodiment, a serotonin precursor, such as L-tryptophan, is also provided. Reduction of serotonergic transmission results in a decrease in the utilization of hypothalamic enkephalin. See Schwartz and Mocchetti, Proc. II World Congr. Biol. Psych., 1986. It is expected that this will in turn depress the dopaminergic system. See Devau, et al., J. Neurochem., 49:665-70 (1987). In the short term, cocaine activates the serotonergic receptors through release of neuronal serotonin. Chronic use of cocaine, however, results in down regulation of CNS serotonin and thus, indirectly, in reduced dopaminergic activity. The serotonin precursor may be used with or without the aforementioned dopamine precursor.

In another preferred embodiment, a precursor of the inhibitory neurotransmitter gamma-aminobutyric acid (GABA), e.g., L-glutamic acid, is also given. To date there is no evidence that c:ocaine per se affects GABAergic activity (i.e., storage, release, or turnover), however, a novel approach to chronic cocaine toxicity may involve the GABAergic pathway.

Repeated cocaine use has been linked to a sensitization of the brain resulting in convulsions. Post, et al., in COCAINE: CLINICAL AND BIOBEHAVORIAL ASPECTS, 107-168, (Uhlenhuth, et al., eds., 1987). It has been found that giving an experimental animal a small dose of cocaine once a day sensitizes its brain to cocaine and progressively lowers the threshold for seizures. After several days of such administration, a small, previously non-convulsive, dose of cocaine produces a convulsive seizure; moreover a high percentage of these seizures result in the death of the experimental animal. This phenomenon is not due to any accumulation of the drug or its metabolites in the body; it represents a true sensitization of the brain to the effects of cocaine. With continued treatment, surviving animals may develop seizures spontaneously—in the absence of cocaine. There seems to be a permanent lowered seizure threshold in the organism, analogous to "kindling," the sensitization to convulsive seizures induced by repeated, small electrical stimulation of the brain. Cocaine induced kindling could explain seizures or death in individuals who repeatedly use small amounts of the drug. It implies that each time an individual uses cocaine, there is a small, but progressive increase in sensitivity of the brain to it. Thus, repeated use of cocaine without experiencing a seizure is no guarantee for continued safety.

GABA as well as GABA agonists, injected intracerebroventricularly, will reduce seizure activity during alcohol withdrawal in rodents. Pozdveyev, V.K. NEUROTRANSMITTER PROCESSES AND EPILEPSY 112 (1983). Also amino oxyacetic acid, ethanolamine-o-sulfate and sodium valproate, which increase GABA content, suppress alcohol withdrawal signs in rodents. Utilization of L-glutamine as a natural way to affect brain GABA levels should significantly reduce the chance of seizure activity in the chronic cocaine abuser.

Cocaine addicts often exhibit various nutritional deficiencies. Consequently, it is preferable to further provide certain vitamins and minerals, particularly pantothenic acid (B5), pyridoxal phosphate (B6), magnesium, calcium, and zinc. Note that vitamin B6 is important as a co-factor in the synthesis of dopamine, serotonin and GABA.

Thus, an endorphinase or enkephalinase inhibitor may be combined with one or more of (a) a dopamine precursor (b) a serotonin precursor, (c) a GABA precursor, (d) an endorphin or enkephalin releaser or (e) replacement vitamins and minerals in order to restore the former cocaine user's neurotransmitter systems (and general health and well being) to normal. In an especially preferred embodiment, all of the foregoing elements are administered to the patient.

The major goals in the treatment of long-term recovery from cocaine abuse should include:

1). recovery of serotonergic and catecholaminergic function.

2). enhancement of opioidergic activity.

3). reduction of neurotransmitter (eg. serotonin, dopamine, norepinephrine) supersensitivity.

4). induction of neurotransmitter subsensitivity.

5). normalization of catecholaminergic (dopaminergic) receptor sites.

6). reduced cocaine-induced sensitization to convulsive seizures.

It has been reported that there is a 400:1 greater risk for cocaine dependence in these patients with a familiar history of alcoholism. Since we have found, as described in our copending application Ser. No. 06/757,733, that endorphinase and enkephalinase inhibitors are useful in the treatment of ethanol abuse, we believe that the compositions of this invention are of particular value in the treatment of patients suffering from both cocaine addiction and alcoholism.

The claims appended hereto are hereby incorporated by reference as a further enumeration of the preferred embodiments.

DETAILED DESCRIPTION OF THE INVENTION

We believe that the substrate for cocaine reward is mediated by regions in the brain, "pleasure centers" or "reward centers," which are high in dopamine. These regions include the dopamine-containing nucleus accumbens, and its projection to limbic structures and frontal cortex. In this regard, it has been observed that if dopamine projections to limbic and cortical areas are lesioned the self-administration of cocaine by animals is greatly reduced. Selective dopamine receptor antagonists, like haloperidol, attenuate or block cocaine self-administration in animals. Similarly, in humans, pre-treatment with dopamine receptor antagonists will block stimulant-induced "euphoria". Additionally, dopamine receptor agonists (eg. apomorphine, Piribedil) have rewarding actions. These and other studies suggest that cocaine reward is mediated via activation of dopamine brain circuits.

Cocaine effects on dopamine containing neurons are such that the acute effects involve dopamine activation while the chronic effects induce dopamine deficit. For example, acute use of cocaine activates dopamine circuits by blocking synaptic re-uptake of dopamine, resulting in increased postsynaptic receptor stimulation as these sites are flooded with dopamine. This action of cocaine is important since it eliminates a major means by which dopamine is conserved and recycled. Norepinephrine, a dopamine metabolite and a reward neurotransmitter in its own right, is also activated.

However, during chronic abuse of cocaine, a shunt is established whereby the net effect leads to a dopamine depletion state. Increased levels of the synaptic dopamine metabolite, 3-methoxytyramine, are found after cocaine administration in animals; receptor affinity changes and brain dopamine levels are decreased after repeated cocaine administration in animals. Similarly, with chronic cocaine use, catecholamines including norepinephrine are depleted and inhibited.

In effect the action of cocaine is as follows: (1) acute blockade of dopamine re-uptake; (2) acute increase in synaptic dopamine; (3) acute increase in dopamine neurotransmission; (4) chronic increase in postsynaptic dopamine receptor number; (5) increased levels of synaptic dopamine metabolites; (6) decreased brain dopamine metabolites; (7) inhibition of dopamine vesicle binding; (8) increased tyrosine hydroxylase activity.

The following definitions may be helpful in the discussion which follows:

Precursor: a compound which, within a reasonable number (preferably 1-4) of metabolic steps, is converted into the transmitter of interest. In some cases, a substance not normally a precursor may be a precursor because of the presence of a second substance blocking the normal metabolic pathway.

Source: the "source" of a substance includes the substance itself as well as its precursors, in pure or impure form.

Inhibitor: an agent which by any of several means, e.g., competitive or non-competitive, reversible or irreversible means, will block the action of the transmitter at the receptor or modulator, or will prevent the action of an enzyme on its substrate. For example, naloxone competitively blocks the action of morphine on the Mu opiate receptor in the brain and promotes the analgesic action of morphine; the agent Parmate(TM) blocks the action of the enzyme MAO on its monoamine substrates.

Releaser: an agent which facilitates or mediates the release of a transmitter.

Agonists: an agent which activates a receptor in a manner analogous to that of the transmitter; also an agent which acts at a modulator site to facilitate the action of the transmitter. Antagonists: an agent which decreases or inhibits the action of the transmitter at its receptor site; to be distinguished from an agent which blocks the action of the effector portion of the receptor-modulator-effector complex.

Restoration of Catecholaminergic System

The catecholamines dopamine (DA), norepinephrine (NE) and epinephrine (E) are all neurotransmitters.

Catecholamines are compounds which possess two adjacent hydroxyl (OH) groups on a benzene ring. In the body, such substances are synthesized form the aromatic amino acid L-tyrosine, wh ich is hydroxylated to L-3, 4-dihydroxyphenylalanine (L-dopa) by the enzyme tyrosine hydroxylase. L-tyrosine is actively take up into noradrenergic nerve terminals. L-phenylalanine is a precursor of L-Tyrosine.

Tyrosine hydroxylase is located in the cytoplasm of noradrenergic neurons and is the rate-limiting enzyme in the synthesis of NE. Extensive research has revealed that reduced pteridine cofactor, molecular oxygen and ferrous ions are all required for activity. In the cytoplasm, L-dopa is decarboxylated to DA by L-aromatic amino acid decarboxylase, an enzyme which requires pyridoxal phosphate (Vitamin B6) as a cofactor. The dopamine (DA) is actively taken up into granular storage vesicles in which the DA is hydroxylated to form norepinephrine (NE) by the enzyme dopamine-Bhydroxylase. This enzyme requires copper, molecular, oxygen and ascorbic acid as a cofactor. In some neurons in the CNS, NE is further converted to epinephrine (E) by the enzyme phenylethanolamine-N-methyltransferase.

Tyrosine hydroxylase activity is influenced by the following: 1. Via "end product" inhibition, increased concentration of NE within nerve terminals decreases the rate of conversion of L-tyrosine into L-dopa.

2. Increased sympathetic activity from the CNS increases the synthesis of NE.

3. Angiotensin II increases the rate of NE synthesis.

4. Agonists (e.g., clonidine) and blockers (e.g., phentolamine) of adreno-receptors change the rate of NE release by mechanisms involving adrenergic receptors located on the presynaptic terminal.

Inhibitors of the enzymes of NE synthesis include: methyl-p-tyrosine (inhibits tyrosine hydroxylase); carbidopa (inhibits aromatic amino acid decarboxylase in tissues outside the CNS); and diethyldithiocarbonate, FAI63 and disulfiram (inhibitors of dopamine-B-hydroxylase).

NE is stored within the nerve terminal in multiple storage complexes and more than one anatomical location. One form of NE storage type is a granular complex found within vesicles in noradrenergic nerve terminals. The granular complex consists of NE bound to ATP, several proteins collectively called chromogranins, includes dopamine-B-hydroxylase and $Mg++$, $Zn++$ and $Cu++$.

The uptake of DA and NE into storage vesicles is an active-transport process which requires ATP as an energy source and $Mg++$ to activate the ATPase enzyme which is $Mg++$ dependent. This $Mg++$-dependent uptake process of NE and DA into storage vesicles is a separate and different process from the neuronal uptake process for NE across the nerve cell membrane, which is an $Na+/K+$-ATPase dependen The stability of the NE-ATP-protein- ion storage complex can be disrupted by some compounds which act as chelators of $Mg++$. This may be linked to the magnesium deficiency sometimes found in chronic cocaine abusers. In this regard, chronic administration of cocaine produces an increase in NE turnover.

Release of NE from nerve terminals occurs by a process of exocytosis, which is calcium dependent, whereby a vesicular membrane fuses with the plasma membrane and the vesicular contents, consisting of NE, ATP, dopamine-Bhydroxylase and chromogranins, are released into the synaptic cleft.

One mechanism known to control the availability of NE to postsynaptic receptors operates by means of presynaptic receptors located on the terminal from which NE is released.

The actions of NE in the synaptic cleft are terminated by removal from the synaptic cleft by an uptake system found on presynaptic nerve endings. There are two types of neuronal uptake of NE—uptake I and uptake II.

Uptake I is energy dependent, requiring ATP which is broken down by a sodium dependent ATPase. This is a high-affinity process, which means that it is efficient at the eliminating low concentrations of NE from the synaptic cleft. The neuronal uptake system transports NE into the nerve terminal. Inside the nerve terminal most of the NE is taken up into storage vesicles. Inhibitors of this process include: cocaine, tricyclic antidepressants, amphetamine and tyramine.

Uptake II involves the accumulation of NE by non-neuronal tissues. High plasma levels of NE derived from stimulation of the adrenal medulla, or intravenous injection of a catecholamine will be removed by uptake into non-nervous tissues such as liver, muscle and connective tissue. The NE or any other catecholamine diffuses back into the circulation or, more commonly is destroyed intracellularly by the enzymes monoamine oxidase (MAO) and catechol-O-methyltransferase (COMT).

MAO is found in all tissues which contain mitochondria, and is bound to their outer membranes. MAO is present in liver, brain, nerves,muscles and all actively metabolizing tissues. It oxidatively deaminates NE to c, 4-dihydroxymandelic acid which can then by O-methylated (by COMT) to give rise to 3-methoxy-4-hydroxy-mandelic acid.

MAO in actuality describes a group of isoenzymes which possess different tissue distributions, substrate specificities, inhibitor characteristics and physical properties. For example, MAO A has a substrate preference for NE and 5HT, and is selectively inhibited by clorgyline. MAO B has a substrate preference for olopamine and phenylethylamine, and is selectively inhibited by deprenyl (selegiline). Other well known MAO inhibitors include iproniazid, nialamide, pargyline, tranclypromine and phenelzine.

COMT is found in large quantity in liver cells. In the CNS, COMT acts on E and NE which has not been inactivated by neuronal re-uptake. Pyrogallol, an inhibitor works by blocking the COMT dependent transfer of a methyl group from S-adenosyl-L-methionine to the hydroxyl group at the 3' position of the catechol ring of NE, E and DA.

Dopamine is the precursor of NE and E, and plays a significant role in the CNS and at some ganglia in the autonomic nervous system.

High intraneuronal amounts of DA inhibits tyrosine hydroxylase by end-product inhibition, thus decreasing the rate of DA synthesis. Furthermore, the rate-limiting step in the synthesis of DA is the conversion of tyrosine to L-dopa by tyrosine hydroxylase. Under normal situations tyrosine hydroxylase is completely saturated with L-tyrosine and thus increase in circulatory tyrosine levels do not increase the rate of DA synthesis. However, this fact changes when there is a deficit in both the amount of DA and when tyrosine hydroxylase is compromised as under the influence of cocaine.

L-dopa is actively taken up into DA neurons in the CNS where it is converted to DA. Following L-dopa therapy there is a significan&ly increase in the amount of DA synthesized and stored. By comparison with the dopaminergic system, there is relatively little increase in the synthesis of NE following L-dopa, treatment.

Dopamine is stored in storage granules where the catecholamine is complexed with chromogranins, divalent metal ions and ATP. DA is believed to be released into the synaptic cleft by exocytosis. As with NE, this is a calcium dependent process and occurs in response to action potentials reaching nerve terminals or to drugs. The following substances can increase DA release; cocaine, (+)-amphetamine, methylamphetamine, tyramine, amantadine, m-phenmetrazine, phentermine and nomifensine. In addition to causing the release of DA, these compounds can also, to different degrees, inhibit neuronal re-uptake of DA.

After DA is released into the synaptic cleft its action is terminated by a neuronal re-uptake system which is a high affinity, energy-dependent active-transport process. The system is similar to that already described for NE. Both MAO and COMT are responsible for the transformation of DA to 3, 4-dihydroxyphenylacetic acid (DOPAC) and homovanillic acid (HVA, 3-methoxy-4-hydroxy-phenylacetic acid), respectively.

Cocaine, by virtue of blocking re-uptake of DA into presynaptic nerve terminals, prolongs the effect of release DA in the synaptic cleft.

Elevation of brain tyrosine levels results in an increase in L-DOPA synthesis in the brain. L-DOPA in turn is metabolized to dopamine. The synthesis and release of dopamine is elevated following tyrosine administration. Without increasing catecholamine levels, dietary tyrosine increases turnover and release of dopamine and norepinephrine. Stress, cold or certain drugs, induce an increase in nerve firing to lower the levels of catecholamines in the nerve terminals.

L-Phenylalanine is an essential amino acid which is also a precursor for the synthesis of the neurotransmitters dopamine and norepinephrine. These neurotransmitters, as measured by their metabolites, HVA, DOPAC, and MHPH, are significantly altered during periods of intense exercise and physical endurance. L-phenylalanine may be used instead or in combination with L-tyrosine or L-dopa to restore dopamine reserves after depletion by cocaine abuse.

The use of these precursors may be supplemented at appropriate stages of treatment with dopaminergic releasers, blockers, agonists or antagonists, or agents affecting the reuptake or degradation of dopamine, norepinephrine or epinephrine. However, and more importantly, the entire range of dopaminergic activity including synthesis, and release is regulated to some degree by certain opioid peptides (e.g. enkephalins and endorphins). Centrally administered opioid peptides (endorphins and enkephalins) produce elevations in levels of catecholamines in blood plasma in animals and humans. Clouet, in OPIOIDS IN MENTAL ILLNESS: THEORIES CLINICAL OBSERVATIONS, AND TREATMENT POSSIBILITIES, Ann N.Y. Acad. Sci., 398: 130-139 (1982). In fact, blockade of presynaptic dopaminergic receptors results in an enhancement of B-endorphin release, showing a unique reciprocal relationship.

Restoration and Enhancement of Opioidergic Action

A particular feature of this invention is the use of substances which inhibit the destruction of neuropeptidyl opiates. These opiates promote the synthesis and release of dopamine. It has been shown that the administration of opiate-like substances to animals increases the rate or striatal DA biosynthesis and metabolism, an effect which is mediated by special opiate receptors located on nigrostriatal dopaminergic terminals: See Clouet, et al., Science 68 : 854-855 (1970); Biggio, et al.; Science, 200: 552-554 (1978); Regiawi, Subs. Alc. Actions/Misuse 1: 151-158 (1980). Upon chronic administration of B-endorphin or enkephalin dopaminergic tolerance develops. Iwatsubo, et al., Biochem, Pharmacol. 24: 1495-1503 (1975); Arden, N. E., J. Pharm., Pharmacol 24: 905-911 (1972). The postsynaptic DA receptor becomes supersensitive in tolerant animals. Schwartz, et al.), Neuropharmacol. 17: 665-668 (1978).

Cocaine also affects opiodergic action. With chronic exposure cocaine to rats, dose-dependent alteration of naloxone binding was observed. Opiate receptor density was significantly decreased in several brain structures, while it was increased in the lateral hypothalamus. It appears that opiate binding was specifically affected in "reward centers" and not in other regions. P. Hammer, Jr., et al., Soci., Neuroscience Abstracts, 13 (21): 85 No. 2710 (Apr. 1987). Furthermore, naloxone, in another study, effectively blocked the threshold lowering action of cocaine in reward centers of the brain. Bain and Korwetsky, Lipo Sci 40: 1119-1125 (1987).

Moreover, cocaine appears to affect the analgesic action of certain opiates. (Misra, A. L. Pontani, R. G. and Vadlamani, pain 2811): 129-38, 1987).

We believe that the reinforcing action of cocaine may be mediated in part by opiate systems in brain reward centers, which are altered by chronic cocaine exposure.

Narcotic drugs were found to act at various "opiate receptors." Later the brain and other nervous tissue were found to possess endogenous opioids (EO). Hughes and his collaborators identified in the brain the related pentapeptides, methionine and leucine-enkephalin. See et al., Nature 258: 577-580, (1975). The enkephalins Hughes activate both delta and mu receptors, while beta endorphin activates the epsilon receptor. Endocrinologists were able to show that B-lipotropin (B-LPH), already recognized as a pituitary hormone, contained the Met-enkephalin sequence of five amino acids, and that B-LPH was hydrolyzed to an active opioid, B-endorphin. See Li, C. H., et al., Proc. Natl. Acad. Sci USA 73: 1145-1148 (1976).

Currently, we know of at least three chemical families of EO's of different origin and with different function, although all peptides contain the sequence Tyr-Gly-Gly-Phe-X at their N-terminals. The endorphin family includes the large precursor, pro-opiocortin, B-LPH, and B-endorphin. The second family of EO's is the enkephalin family. Both [Met]enkephalin and [Leu]-enkephalin are derived from a large peptide precursor containing both sequences. Hexa- and hepta- peptides with one or two basic amino acids attached to the carboxyl end of enkephalin, and a hepta peptide; [Met]enkephalin-Arg-Phe seem to be naturally occurring intermediates. Hexum, et al., Life Sci 24: 1211-1216 (1980). The third family are kappa agonists, such as dynorphins 1-13 and 1-17. These CNS components antagonize morphine actions. Dynorphin may act as a precursor of Leu-enkephalin which forms the N-terminus; conversion to the subendorphin form (E5) will then result in altered receptor affinity (kappa to delta), illustrating a possible new regulatory role for enzyme modulating ligand expression.

Peptides from each family seem to act both as neurotransmitters and as neurohormones. The pentapeptide enkephalins are localized in nerve terminals and are released from neurons upon stimulation. Leu- and Met-enkephalins are released from the adrenal medulla into the blood and act as neurohormones. Beta-endorphin is released from the pituitary gland into blood and it may act as a neurotransmitter in discrete areas of the brain. Bloom, F. E., et al., Proc. Natl. Acad. Sci., USA 75: 1591-1595 (1978). Both endorphins and enkephalins produce biochemical and pharmacological responses, including tolerance, dependencies and abstinence, similar to those produced by narcotic analgesic drugs when the EO's are administered to man or animals. The endogenous opiates, like the narcotic drugs, are members of the class "opioids." Enzymes which degrade enkephalins (E5) are generally called "enkephalinases."

It is well established that tissues contain a variety of peptidases which metabolize pentapeptididyl enkephalins (E5). Enzymes acting as enkephalinases include soluble and particulate bound aminopeptidases Hersh, Biochem 20:2345-2350 (1981) and others acting at the Gly3-Phe4 site such as peptidyl dipeptidases or metalloendopeptidases Benuck, et al. Biophys Res Comm 107:1123-1129, 1982; Schwartz, et al. Adv Biochem Psychopharmacol 22:219-235 (1980). The metalloenzyme carboxypeptidase A cleaves enkephalin leaving Tyr-Gly-Gly-C and the terminal dipeptides Met-Phe or Leu-Phe. Unlike the biogenic amines, for which a single enzyme is largely responsible for inactivation at the target site, degradation of the enkephalins involves multiple enzymes, although the metalloendopeptidase would appear to be the principal enkephalinase.

The scheme below illustrates the sites of action of enzymes associated with the degradation of E5.

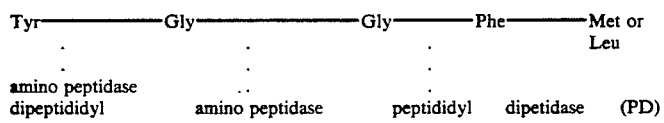

```
Tyr————————Gly————————Gly————————Phe————————Met or
                      .            .                        Leu
                      .            .
amino peptidase       ..           .
dipeptididyl     amino peptidase   peptididyl   dipetidase   (PD)
```

One strategy to deal with the degradation is to provide E5 surrogates. For enkephalin, several chemical modifications are required to block degradation by tissue enzymes. These include: a) modification of N-terminal-Tyr inasmuch as tyrosine-modified analogs of methionine enkephalinase resist degradation (Coy and Kastin, J Peptides 1:175-177 (1980); b) presence of a D-amino acid in position 2 to blook effects of amino peptidases: and/or c) modification or presence of a D-amino acid in positions 3-5 to block action of peptidyl dipeptidases or other enzymes acting at the Gly3—Phe4 bond.

Other analogs could include D-Ala-enkephlamide or FK 33-824, as mu agonists; delta agonists such as enkephalin-Arg-Phe; and dynorphin 1-13 or 1-17, which are kappa agonists (Wisler et al, 1981).

It is unknown at the present time whether these agents, which are candidate E5 agonists, have potential addiction liability, tolerance and other toxicological problems associated with their clinical use. The probable addictive nature of many of these modified, enzyme resistant surrogates would significantly reduce their clinical application.

A second, and preferred strategy to enhance enkephalin or endorphin action in vivo is to use specific enzyme inhibitors. Certain enkephalin fragments (Gly-Gly-Phe-Met or Gly-Gly-Phe-Leu, Phe-Met, Phe-Leu) can act as inhibitors of enkephalin and it is likely that larger enkephalin-type forms themselves also have inhibitory properties.

In this invention the term "enkephalinase inhibitors" includes but is not limited to D-Phenylalanine (DPA), DL-Phenylalanine (DLPA), hydrocinnamic acid, and D-amino acids such as D-Leucine. It is anticipated that other enkephalinase inhibitors selected from a group consisting of certain protein synthesis inhibitors (bacitracin, bestatin, and puromycin), peptide amino acids (free, D-form monoamino acids, di-and tripeptides of the essential amino acids in the D-form, th iol benzyl amino acids, (e.g., 2-[mercapto-3-phenylpropanoyl]-L-Leucine), carboxyl alkyl methyl' esters, N-[(R,S)-2-carbethoxy-3-[phenyl propanol]-L leucine), benzomorphan-enkaphalins, and other, structurally unrelated compounds such as secobarbital, pyrophosphate, o-phenanthroline, phosphamidon, Z-leucine-NHOH, and Z-glycine-NHOH. Dipeptides D-Phe-D-Leu and D-Phe-D-Met and the polypept.ide L-Tyr-Gly-Gly-D-Phe-D-Leu and L-Tyr-Gly-Gly-D-Phe-D-Met, together with D-Phe, D-Leu, and hydrocinnamic acid, are of particular interest.

D-phenylalanine has been known to inhibit carboxypeptidase A (Hartruck, JA, and Lipscomb, WN: Carboxypeptidase A: in THE ENZYMES 1-56, (Boyer, ed. Academic Press, New York, 1971)) and more recently has been shown to possess analgesic properties (Ehrenpreis, S., et al., Pharmacologist 20:168, (1978) and Della Bella, et al., Neuropharmacology 18:718:721, (1979) as well as antidepressant action (Beckmann, et al., J. Neuronal Trans. 41:123-124, (1977)).

To evaluate the potency of D-phenylalanine as an inhibitor of enkephalinases it was shown that the compound indeed significantly reduced degradation of the oligopeptides (D-Ala2-D-Leu5) enkephalin (DAPLE) and Tyr-D-Ala-Gly-Phe (TAAGP), in rat intestinal mucosa. Gail, A. et al., J. Pharmacol. Exp. Therap. 226:111 33-38, (1983). However, D-phenylalanine was much less effective when studied in vitro for inhibitory activity against both enkephalinase A and enkephalinase B activity obtained from calf brain. Amsterdam, et al., Life Sci., 33(1) 109-112, (1983). Interestingly, the addition of just one amino acid to form the dipeptide D-Phe-Tyr markedly enhances the inhibitory potency.

D-phenylalanine has been shown to inhibit the degradation of both enkephalins and B-endorphin. It works better on the enzymes regulating enkephalin breakdown as compared to the enzymes regulating B-endorphin. Its activity is also tissue-specific; in the hypothalamus, enkephalinase is 80% inhibited and endorphinase 5%; in the cortex, enkephalinase 60%, but endorphinase only 18%; in the striatum, enkephalinase 78% and endorphinase 10%; and, in the spinal cord, enkephalinase 84%, endorphinase 40%. Ehrenpreis, et al., In: ADVANCES IN ENDOGENOUS AND EXOGENOUS OPIOIDS: PROC INTL NARCOTIC RES CONF, KODANCHA, TOKYO, 279-281, (1981). Other studies showed actual CNS increases of [Met]-enkephalin tripled within 90 minutes following DPA injection and remained high six days later. Balagot, R., et al., In: ADVANCES IN PAIN RESEARCH AND THERAPY, Vol. 5, 289-293 (Bowica, EUJ, et al., Raven Press, New York, 1983). Other increases of [Met]-enkephalin in the brain of mice was similarly found with hydrocinnamic acid, a known metabolite of D-phenylalanine.

A further enhancement is to combine an enkephalinase inhibitor with an enkephalin releasing agent. The rationale for this is that by doing so we could significantly enhance the effect of enkephalin on its respective opiate receptor sites (eg., del&:a or mu). To accomplish this aim we would prefer to use the peptide Tyr-Arg (Kyotorphin), or its stable analog, Tyr-D-Arg, which has been shown to be analgesic and to enhance intracellular calcium in synaptosomes in rat brain striatal slices. These substances appear to be putative methionine-enkephalin releasers acting by an unknown mechanism Ueda et al. Biochem. Biophys. Res. Comun. 137:897, (1986).

To provide both enkephalinase inhibition as well as enhanced neuronal enkephalin release the substance known as Kyotorphin (Tyr-Arg) may be used at a daily dosage range of 15 ug-15 mg. Cf. Takagi, et al., Eur. J. Pharm., 55:109 (1979). The more stable analog Tyr-D-Arg, at a daily dosage range of 15 ug-15 mg may be substituted as a enkephalin releaser. Cf. Tajima, et al., Chem. Pharm. Bull., 28:1935 (1980); Ueda, et al., Biochem. Biophys. Res. Commun., 137: 897–902 (1986).

Thus, an enkephalin releaser may be combined with an enkephalinase inhibitor to achieve a high degree of enkephalinergic activity at the synapse to further augment the release of reuronal dopamine. This will act as a form of "replacement therapy" and reduce "craving" for cocaine. This treatment will be most useful during the 12 months following cocaine detoxification.

Restoration of Serotonergic System

Serotonin (5-hydoxytryptamine, 5HT) is a CNS neurotransmitter. It is also found in the enterochromaffin system of the intestine, and in blood platelets.

This neurochemical is biosynthesized by first hydroxylating L-tryptophan to obtain 5-hydroxytryptophan and then decarboxylating the latter to obtain serotonin. the hydroxylation (the rate-limiting step) is performed by the enzyme tryptophan hydroxylase, while the decarboxylation is accomplished by the ubiquitous enzyme L-aromatic acid decarboxylase. This enzyme requires pyridoxal phosphate as a cofactor.

Serotonin is metabolized into 5-hydroxyindole-acetic acid by monoamine oxidase. This metabolite is then excreted in the urine.

Central brain serotonin mechanisms may be important in the control of mood and behavior, motor activity, feeding and control of hunger, thermoregulation, sleep, certain hallucinatory states, and possibly some neuroendocrine control mechanisms in the hypothalamus.

Chronic use of cocaine reduces concentrations of serotonin and its metabolite. Cocaine apparently reduces uptake of the serotonin precursor tryptophan, thereby reducing serotonin synthesis. Cocaine also reduces tryptophan hydroxylase activity. Thus, cocaine decreases serotonergic action. Reith, et al., Brain Res. 342(1): 145–8 (1985).

Treatment of rats with drugs which deplete serotonin (Fenfluramine, PCPA or 5-7-DHT) increased the content of both enkephalin and endorphin in the hypothalamus but not in the brain regions. Since there was no alteration in content of either mRNA or the precursors- pro-enkephalin (PE) or propiomelanocortin, it was suggested that serotonergic transmission requlates opioid peptide utilization without affecting synthesis. Schwartz, et al., Fourth World Congress on Biological Psychiatry, 418, No. 600.2 (1985).

This finding supports the hypothesis that lowered release of enkephalin would result in a reduced dopamine activity manifest as a depressive state. Following intense exercise, certain behavior deficits occur which include pain, depression and sleep disorders. Restoration of the serotonergic transmission with L-Tryptophan should help restore positive mood.

Moir and Eccleston, J Neurochem 15:1093 (1968), found that providing tryptophan in the diet, i.e., precursor loading, had a definite effect on the cerebral metabolism of serotonin and related compounds. Brain serotonin content can depend upon the plasma tryptophan levels. Fernstrom and Wurtman, Science 174:1023 (1971). Rats fed tryptophan-poor diets had low serotonin levels in the brain, and L-tryptophan restored this deficiency. If tryptophan was injected into the bloodstream, the levels of tryptophan and serotonin in the brain were elevated nine- and two-fold, respectively. Infusion of tryptophan in neurological patients with both depression and insomnia resulted in six-fold elevations in cortical tryptophan levels. Gillman et al., J Neurochem, 37:410 (1981).

Lieberman et al., J Psych Res 17:135 (1983) compared tryptophan (50 mg/kg) and tyrosine (100 mg/kg) or placebo in a double-blind crossover experiment in eight healthy men. Tryptophan, but not tyrosine, significantly reduced pain discriminibility. Other studies revealed that tryptophan reduced clinical pain (Seltzer et al. 1983): prevented migraine (Poloni et al. Experientia 30:640, 1974): and, reversed analgesic tolerance. Hosobuchi, et al. in NEURAL PEPTIDES & NEURONAL COMMUNICATIONS, 563 (1980). It would appear that tryptophan via serotonergic activation results in enhanced endorphinergic release which results in analgesia.

Unlike tyrosine hydroxylase, under normal physiological conditions, tryptophan hydroxylase is not saturated, i.e., the enzyme is not working to full capacity and thus tryptophan hydroxylase activity is significantly affected by L-tryptophan. The amount of available free L-tryptophan is dependent on a number of factors including the concentration of circulating L-tryptophan in the plasma at the rate of its uptake in the brain and presynaptic terminals. We contemplate using L-tryptophan to restore the serotonergic system disrupted by cocaine.

5HTP is not as useful as a therapeutic agent. The rate of entry of L-tryptophan into the brain depends upon the ratio of free-bound tryptophan in the plasma, and this ratio is influenced by the concentration in the blood of neutral amino acids, insulin and pharmaceutic agents, which compete for the plasma protein binding sites, as well as for the tryptophan-uptake sites. Also, 5HTP is taken up by neurons other than just 5HT neurons; therefore the increases in 5HT synthesis are not selectively limited to serotonin neurons.

Inhibitors of enzymes involved in 5HT synthesis include irreversible tryptophan hydroxylase inhibitors (DL-parachlorophenylalanine, 6-Flurotryptophan and L-propyldoracetamide) and inhibitors of 5HTP decarboxylase (carbidopa and 1-methyl-5HTP).

Serotonin can be released into the synaptic cleft by the process of exocytosis in response to action potentials and to drugs. Facilitation of 5HT release can be accomplished with cocaine, (+)-amphetamine, methamphetamine, fenfluramine, parachloramphetamine, clorimipramine (clomipramine) and amitriptyline.

Three types of 5HT receptors (5HT-1, -2 and -3) have been proposed. 5HT receptor agonists include LSD, quipazine, N,N-dimethyl-tryptamine (DMT). 5HT receptor antagonists include cyproheptadine, methysergide, LSD, 2-bromo-CSD (BOL), ketanserin, xylamidine, cinanserin and 1-(−)-cocaine.

Inactivation of 5HT involves high-affinity energydependent active-transport mechanism which exists to remove 5HT from the synaptic cleft back into the presynaptic neuron.

Inhibitors of neuronal uptake of 5HT include the tricyclic anti-depressants (imipramine, desimipramine, amitriptyline, chlorimipramine, fluvoxamine; fenfluramine [an anorectic agent] and cocaine. Any 5HT not bound in storage will be converted into metabolites by MAO. However, if MAO is inhibited, serotonin is metabolized to N-Methyl, or N-N-dimethyl by O-methyltransferase (COMT).

Restoration of GABAergic System

GABA is an inhibitory neurotransmitter which controls the release of dopamine. Gessa, et al., 4th World Congress on Biological Psychiatry, 459 No. 620.10 (1985). As previously stated, it seems to reduce seizure activity during alcohol withdrawal.

The main synthetic pathway to gamma-aminobutyric acid (GABA) is via decarboxylation of L-glutamic acid by glutamic acid decarboxylase (GAD). Like other amino acid decarboxylases, this enzyme needs Vitamin B6 (pyridoxal phosphate) as a cofactor. GAD is found exclusively in the cytoplasm of synaptic GABA nerve terminals. The basic control of GABA synthesis is GAD which seems to be the rate limiting step in GABA synthesis. GABA can influence FAD activity by end-product inhibition. Saturation concentrations of L-glutamic acid are present in the presynaptic neuron; thus, increased substrate concentrations do not normally affect the rate of GABA synthesis. Therefore, the exogenous administration of L-glutamic acid may not significantly increase the neurotransmitter GABA, unless L-glutamic acid levels are abnormally low. However, it has been shown that a 10 day administration of glutamine (500 ng/kg, per day) with the drinking water to adult albino rats with different alcohol motivation resulted in a significant increase in the content of glutamate, GABA and taurine in the brain. Glutamine is an active intermediate in transport of ammonia from the brain and therfore may greatly affect catabolism of different amino acids in nervous tissue. (Ostrovsky, Substance Alc. Actions/Misuse 5: 247-253 (1984). After deamination, glutamine may become a precursor of glutamate and, accordingly, GABA. Thawki, et al., J. Neurochem 41: 611-617 (1983).

There are at least two types of GABA receptors; 1) GABAA receptor sensitive to the competitive blocking action of bicuculline and picrotoxin or picrotoxinin. These receptors are on postsynaptic structures and mediate classical inhibitory actions of GABA; 2) GABA-B receptors are located on presynaptic terminals and these receptors are insensitive to the blocker actions of bicuculline. GABA-B receptors can modify release of not only GABA in the CNS, but also NE from certain sites in the sympathetic nervous system.

It has been suggested that certain clinical malfunctions may be associated with GABA systems such as movment disorders, Huntington's chorea, epilepsy and alcoholism. Changes in affinity of GABA receptors for GABA, the benzodiazepine binding sites for benzodiazepines and or the barbiturate binding site for barbiturates is regulated by a protein "GABA-modulin." GABA-modulin, is similar to GTP regulator protein associated with receptors linked to adenylate cyclase. The activity of GABA-modulin is determined by phosphorylation.

GABA is typically associated with short inhibitory neurons in the hypothalamus, hippocampus. basal ganglia of the brain, substantia gelatinosa of the dorsal horn of the spinal cord and in the retina. Some long-axon pathways within the CNS have been identified.

GABA agonists include imidazole acetic acid, 3-aminopropane sulphonic acid, and THIP (4,5, 6, 7, -tetrahydro -isoyazolo-[415-C]-pyridin-3-ol, and muscimol (3-hydroxy-5-amino-methylisoxazole) which is found in amanita muscaria.

GABA antagonists include bicuculline, picrotoxin, picrotoxinin and benzylpenicillin.

There is a high-affinity sodium dependent uptake system present in presynaptic GABA nerve terminals and glial elements which inactivate released GABA by removing it from the extracellular space.

Inhibitors of GABA uptake include, for the neuronal uptake type, diaminobutyric acid and cis-2, 3aminocyclohexane, carboxylic acid; for the glial uptake type B-alanine; and for the miscellaneous uptake type, nipecotic acid, benzodiazepines, neuroleptics and tricyclic antidepressants.

GABA, taken back into the presynaptic neuron after release and receptor interaction, is recycled as a potentially reuseable transmitter. GABA is enzymatically metabolized in both the nerve terminal and glial tissue and converted, in the presence of A-oxoglutamic acid, to succini semialdehyde by the mitochondrial enzyme GABA aminotranferase (GABA-T). The succinic acid which is formed enters the tricarboxylic acid (Krebs) cycle. GABA-T requires pyridoxal phosphate as a cofactor. Succinic semialdehyde is rapidly oxidized to succinic acid by the enzyme succinic semialdehyde dehydrogenase which also involves NAD and NADH as co-factors. Our fomulation for cocaine takes this fact into account by adding pyridoxal-5-phosphate as a promoter of the oxidative-reductive pathway.

In this regard, GABA concentrations can be increased by the administration, to animals, of the following inhibitors of GABA-T: ethanoloamine-P-sulphate, gamma acetylenic GABA, gamma vinyl GABA, gabcuculline, hydazinopropionic acid, sodium di-N-propylacetate (sodium valproate) and aminooxyacetic acid (inhibitor of Vitamin B6) (Bloom. FE, In: THE PHARMACOLOGICAL BASIS OF THERAPEUTICS, 247-248, (Goodman, et al., eds., 1985).

No reports to date have suggested that precursors of GABA are useful in the treatment of cocaine abuse. We believe that since the GABA system inhibits the release of dopamine, a GABA precursor may reduce the severity of the dopamine depletion associated with cocaine. In addition, as mentioned earlier, we believe it can reduce seizure propensity.

The invention will be more fully understood from the following examples.

EXAMPLE I

An example of an amino acid formulation for treating cocaine addiction is as follows:

| Ingredient | per capsule (mg) | daily dose (mg) |
|---|---|---|
| DL-phenylalanine | 250 | 1500 |
| L-tyrosine | 150 | 900 |
| L-tryptophan | 50 | 500 |
| L-glutamine | 50 | 300 |
| zinc | 5 | 30 |
| magnesium | 25 | 150 |
| calcium | 25 | 150 |
| thiamine | 30 | 100 |
| riboflavin | 2 | 15 |
| niacinamide | 30 | 100 |
| pantothenic acid | 5 | 90 |
| pyridoxal phosphate | 5 | 20 |
| buffered ascorbic acid | 100 | 600 |
| folic acid | 60 | 400 |
| cyanocobalamin | 1 mcg | 6 mcg |

While the foregoing doses are preferred, it is contemplated that the quantities of each ingredient may be varied by an order of magnitude (10% to 1000%). Because of the interactions of the various neurotransmitters, an increase in the amount of one ingredient may facilitate the reduction of another ingredient. Also, other substances of similar activity, as noted above, may be substituted for those of this Example.

D-phenylalanine inhibits carboxypeptidase A, an enzyme contributory to the degradation of enkephalins, thereby increasing enkephalin activity. L-Phenylalanine and L-Tyrosine are precursors of the catecholamine neurotransmitters dopamine and norepinephrine. L-Tryptophan is a precursor to serotonin. L-Glutamine contributes to the maintenance of the inhibitory neurotransmitter gamma-aminobutyric acid (GABA). Zinc is essential for protein synthesis and in the action of many enzymes. Magnesium plays a role in the manifestations of stress and promotes well-being. Calcium is a required substance for proper neurotransmitter release and function. Thiamine promotes the synthesis of niacinamide and enhances oxidative metabolism of brain cells. Riboflavin is a cofactor which acts as a hydrogen acceptor and promotes the conversion of tryptophan to niacinamide. Niacinamide is an essential part of the enzyme system concerned with efficient use of oxygen by neurons and promotes brain cell respiration. Pantothenic acid is a vital substance involved in cellular metabolism (i.e. acetyl transfer). It is believed that together, thiamine, riboflavin, niacinamide and pantothenic acid reduce irritability, restlessness and fatigue. Pyridoxal-5-phosphate facilitates the absorption of many amino acids and acts as a cofactor in the synthesis of these transmitters. Cyanocobalamin is a cofactor/coenzyme for both chemical synthesis and neuronal electrical activity. Ascorbic acid is involved in the metabolism of phenylalanine and tyrosine. Folic acid promotes oxidation in the blood as a hematopoietic agent.

Similar to its use in cocaine abusers, ascorbic acid (vitamin C) affects the opioid receptor system and reduces opiate and alcohol withdrawal reactions as well as its combination with DL-Phenylalanine in a number of patients, has resulted in reduced alcohol craving.

Niacinamide, 3-pyridine carboxamide, affects the anxiety state of the individual and has a positive effect during alcohol withdrawal. It is believed to affect the opioid receptor system.

The formulation of Example 1 was administered to 26 cocaine dependent subjects under treatment for cocaine addiction. One month after release, only three had reverted to using cocaine. Within five days, experimental patients exhibited (as compared to control patients) a decided decrease in agitation, outside focus and most importantly drug hunger. There was much less acting out and less craving. The vital signs were more stable with a reduction in sympathetic discharge, i.e., the severity of the cocaine "crash" was reduced. Normally, viewing street corners associated with drug traffic and drug dealers' houses, produces agitation in patients. With our treatment this was greatly reduced. The patients were also more cooperative.

It will be recognized that while this invention is directed to the use of a substance which inhibits the destruction of endogenous neuropeptidyl opiates, especially in combination with dopamine, serotonin and/or GABA precursors, it may be also be beneficial to add various neurotransmitter agonists, blockers, antagonists, releasers, or degradation inhibitors.

It may also be desirable to modulate cholinergic transmission with appropriate agonists, antagonists, precursors, releasers, or degradation inhibitors. There is some evidence that cocaine causes non-competitive inhibition of the cholinergic system. See Karpen, et al., PNAS (USA), 79: 2509-13 (1982); Karpen, et al., Biochemistry, 25: 1777-85 (1986).

We claim:

1. A method for treating cocaine addiction which comprises administering to a subject an opiate destruction-inhibiting amount of at least one substance which inhibits the enzymatic destruction of neuropeptidyl opiates, said substance being selected from the group consisting of:
   (i) hydrocinnamic acid,
   (ii) D-form mono amino acids,
   (iii) thiolbenzyl amino acids,
   (iv) di- and tripeptides of essential amino acids in D-form
   (v) enkephalin fragments,
   (vi) oligopeptides or polypeptides comprising the dipeptides
   D-Phe D-Leu or D-Phe.D-Met
   and (b) a neurotransmitter synthesis-promoting amount of at least one neurotransmitter precursor selected from the group consisting of the dopamine precursors L-Phe, L-dopa and L-Tyr, the serotonin precursors 5-hydroxytryptophan and L-Trp, and the GABA precursors, L-Gln, L-glutamic acid and L-glutamate,
   the amount of said substance and said neurotransmitter precursor being chosen so that said composition is effective in reducing the subject's craving for cocaine.

2. A method for treating cocaine addiction which comprises administering to a subject an opiate destruction-inhibiting amount of at least one substance which inhibits the enzymatic destruction of neuropeptidyl opiates, said substance being selected from the group consisting of:
   (i) amino acids,
   (ii) peptides, and
   (iii) analogues or derivatives of (i) or (ii) above,
   and (b) a neurotransmitter synthesis-promoting amount of at least one neurotransmitter precursor selected from the group consisting of the dopamine precursors L-Phe, D-dopa and L-Tyr, the serotonin precursors 5-hydroxytryptophan and L-Trp, and the GABA precursors, L-Gln, L-glutamic acid and L-glutamate, the amount of said substance and said neurotransmitter precursor being chosen so that said composition is effective in reducing the subject's craving for cocaine.

3. The method of claim 2 wherein the composition comprises at least one dopamine precursor.

4. The method of claim 2 wherein the composition comprises at least one serotonin precursor.

5. The method of claim 2 wherein the composition comrpises at least one GABA precursor.

6. The method of claim 2 wherien the composition consists essentially of an enkephalinase inhibitor, a dopamine precursor, a serotonin precursor and a GABA precursor.

7. The method of claim 2 wherein the composition consists essentially of D-Phe, L-Phe, L-Tyr, L-Trp and L-Gln.

8. The method of claim 1 wherein the inhibitory substance is administered in a daily dose of 150-15,000 mg, the neurotransmitter precursor is selected from the group consisting of L-Tyrosine, L-Tryptophan and L-Glutamine, and the neurotransmitter precursor is administered in a dialy dose of 9-90,000 mg for L-Tyrosine, 5-5,000 for L-Tryptophan, and 3-30,000 for L-Glutamine.

9. The method of claim 2 wherein the inhibitory substance is administered in a daily dose of 150-15,000 mg, the neurotransmitter precursor is selected from the group consisting of L-Tyrosine, L-Tryptophan and L-Glutamine, and the neurotransmitter precursor is administered in a daily dose of 9-90,000 mg for L-Tyrosine, 5-5,000 for L-Tryptophan, and 3-30,000 for L-Glutamine.

10. A pharmaceutical composition for the treatment of cocaine addiction which consists essentially of (a) an opiate destruction-inhibiting amount of at least one substance which inhibits the enzymatic destruction of a neuropeptidyl opiate, said substance being selected from the group consisting of (i) amino acids, (ii) peptides, and (iii) analogues or derivatives of (i) or (ii) above, and (b) a neurotransmitter synthesis-promoting amount of at least one neurotransmitter precursor selected from the group consisting of the dopamine precursors L-Tyr, L-Phe and L-dopa, the serotonin precursors L-Trp and 5-hydroxytryptophan, and the gamma amino butyric acid (GABA) precursors L-glutamine, L-glutamic acid and L-glutamate, the amount of said substance and said neurotransmitter precursor being chosen so that the composition is effective in reducing the subject's craving for cocaine.

* * * * *